United States Patent [19]

Hargis

[11] Patent Number: 4,605,766

[45] Date of Patent: Aug. 12, 1986

[54] ALKYLATION PROCESS

[75] Inventor: Duane C. Hargis, Baton Rouge, La.

[73] Assignee: Ethyl Corporation, Richmond, Va.

[21] Appl. No.: 650,807

[22] Filed: Sep. 14, 1984

Related U.S. Application Data

[63] Continuation-in-part of Ser. No. 564,749, Dec. 22, 1983, abandoned.

[51] Int. Cl.$^4$ .............................................. C07C 85/24
[52] U.S. Cl. .................................................... 564/409
[58] Field of Search ........................................ 564/409

[56] References Cited

U.S. PATENT DOCUMENTS

| | | | |
|---|---|---|---|
| 3,654,331 | 4/1972 | Klopfer | 564/409 X |
| 3,868,420 | 2/1975 | Evans et al. | 564/409 |
| 4,329,517 | 5/1982 | Taniguchi et al. | 568/804 |
| 4,351,958 | 9/1982 | Takahata et al. | 564/409 |
| 4,359,591 | 11/1982 | Fremery et al. | 568/804 |

FOREIGN PATENT DOCUMENTS

| | | | |
|---|---|---|---|
| 53-90227 | 8/1978 | Japan | 564/409 |
| 275377 | 2/1927 | United Kingdom | 564/409 |

*Primary Examiner*—Paul F. Shaver
*Attorney, Agent, or Firm*—Donald L. Johnson; John F. Sieberth

[57] ABSTRACT

Alkylation of aromatic amines with ethers in the presence of iron oxide catalysts is described. By means of the process aniline, o-toluidine, and the like can be selectively orthoalkylated with such ethers as dimethyl ether, diethyl ether, tetrahydrofuran, and 1,4-dioxane at elevated temperatures in the presence of a catalyst containing iron oxide. With ethers such as dipropyl ether, diisopropyl ether and dibenzyl ether, N-alkylation is the predominant reaction. By appropriately modifying the iron oxide catalyst the process can be rendered selective for the para-alkylation of the amine. An advantage of the process is that the unreacted ether is not extensively decomposed in the process and thus can be recovered for recycle or other use.

39 Claims, No Drawings

ALKYLATION PROCESS

REFERENCE TO PARENT APPLICATION

This is a continuation-in-part of prior copending application Ser. No. 564,749 filed Dec. 22, 1983, now abandoned.

FIELD OF THE INVENTION

This invention relates in general to a process for the alkylation of aromatic amines. The alkylated aromatic amines formed by the process are useful as intermediates for producing pharmaceuticals, pesticides, stabilizers, dyestuffs, and the like.

BACKGROUND

Numerous methods, processes, and catalysts have been described for alkylating aromatic amines to provide valuable intermediate products. In general, however, these previous suggestions have one or more defects including lack of selectivity for the desired product, poor conversion of the aromatic amine, and excessive deterioration of the alkylating agent which then cannot be recovered for recycle or other use.

SUMMARY OF THE INVENTION

By the process of the present invention, I have found that aromatic amines having at least one free ortho position may be substituted in the ortho position by catalytic reaction with an ether whereby the remainder of the ether not reacting to alkylate the aromatic amine passes through the reaction undecomposed and may be readily recovered for recycle or other use. In addition, the process can provide a good yield of ortho alkylated product and is usually selective for orthoalkylation of the aromatic amines. The process is suitable for use with catalysts which are easily prepared, have superior catalytic activity, and have long catalyst lives. Moreover, the process gives reproducible results with given reactants, catalysts and reaction conditions.

The catalysts for the process comprise those containing an iron oxide, notably ferric oxide.

The aromatic amine reactants used in the foregoing process are ortho-alkylatable, i.e., they have a ring position ortho to an amino or substituted amino substituent wherein such ortho ring position is unsubstituted except for H. In short, such aromatic amines have a hydrogen atom in at least one of the ortho positions with respect to an amino or substituted amino group thereof.

It has also been found pursuant to this invention that the catalytic process can be used to produce, again on a highly selective basis, N-alkylated aromatic amines from primary aromatic amines either by employing an ether like dipropyl ether or diisopropyl ether, or by employing a primary aromatic amine in which both of the ortho positions are substituted for example with alkyl groups. In these cases as in the orthoalkylation process of this invention, a substantial portion of the remainder of the ether not consumed in alkylating the aromatic amine passes through the reaction undecomposed and is thus available for recovery and recycle or other use.

Yet another facet of this invention is the discovery that it is possible to achieve a substantial extent of N-alkylation of an ortho-alkylatable and N-alkylatable aromatic amine even with ethers like diethyl ether and iron oxide catalyst systems that normally tend to orthoalkylate such amines. This can be accomplished by using a ferric oxide catalyst that during its formation has been precipitated from aqueous solution in the presence of a reagent such as urea. Example III hereinafter illustrates such a preparative procedure (Catalyst G) and the selectivity with which such urea-precipitated catalysts can cause N-alkylation of primary aromatic amines with diethyl ether, and probably dimethyl ether as well. As before, most if not all of the unreacted ether remains unaffected and is available for recovery and recycle or other use.

Still another discovery of this invention is that it is possible to modify the catalyst so that the alkylation of aromatic amines can be focused upon the para position of aromatic amines having an alkylatable para position, even though one or both ortho positions and the amino nitrogen atom(s) are likewise substituted only by hydrogen atoms. To achieve this result the catalyst is modified by supporting it on carbon in suitable form and quantity. Once again, little ether decomposition to uncondensible gases occurs and the unreacted ether can be recovered for recycle or other use.

Thus in a process for alkylating an aromatic amine in the presence of an iron oxide catalyst at elevated temperature, the present invention provides the improvement which comprises alkylating an alkylatable aromatic amine with an ether co-reactive there-with whereby substantially all of the ether not reacting to alkylate the amine remains undecomposed. Preferably, the undecomposed ether is recovered.

In one of its embodiments this invention is a process for producing an orthoalkylated amine comprising the step of, at elevated temperature, reacting an ortho-alkylatable aromatic amine with an ether co-reactive therewith in the presence of an iron oxide catalyst whereby a portion of said ether orthoalkylates the aromatic amine and a substantial portion of the remainder of said ether remains undecomposed. The undecomposed ether may be, and preferably is, recovered or recycled to the process.

In another embodiment the present invention involves orthoalkylating an aromatic amine having a hydrogen in at least one of the ortho positions, by passing said amine along with a suitable ether reactant, preferably in a vapor phase process, over a catalyst comprising predominantly ferric oxide, preferably at about 300°–500° C., whereby a portion of said ether orthoalkylates said amine and a predominant portion or substantially all of the unreacted ether passes over said catalyst undecomposed, and separating and recovering the orthoalkylated amine and the undecomposed ether. Most preferably the recovered ether is recycled to the alkylation reaction zone, either in a continuous process or in a subsequent batch operation.

A further embodiment of this invention is a process which comprises alkylating an aromatic amine having at least one and preferably two hydrogen atoms on an amino group (i.e., an N-alkylatable primary or secondary aromatic amine) by reacting the amine with an ether like dipropyl ether or diisopropyl ether, preferably in a vapor phase process, in the presence of an iron oxide catalyst whereby a portion of said ether N-alkylates the aromatic amine and a substantial portion of the remainder of said ether remains undecomposed. The undecomposed ether may be, and preferably is, recovered or recycled to the process.

In yet another embodiment of this invention a product enriched in N-alkylated aromatic amine is produced by alkylating an aromatic amine having at least one and preferably two hydrogen atoms on an amino group and an inert substituent other than H in each substitutable ortho position relative to the amino group by reacting such amine with an ether co-reactive therewith, preferably in a vapor phase process, in the presence of an iron oxide catalyst whereby a portion of said ether N-alkylates the aromatic amine and a substantial portion of the remainder of said ether remains undecomposed. As above, the undecomposed ether may be, and preferably is, recovered or recycled to the process.

A further embodiment of this invention is a process which comprises alkylating an N-alkylatable aromatic amine, particularly an amine which is also ortho-alkylatable, by reacting the amine with any ether co-reactive therewith, but particularly dimethyl ether or diethyl ether, preferably in a vapor phase process, in the presence of a urea-precipitated iron oxide catalyst whereby a portion of said ether N-alkylates the aromatic amine and a substantial portion of the remainder of said ether remains undecomposed. The undecomposed ether may be, and preferably is, recovered or recycled to the process.

Still another embodiment of this invention is a process for producing a product enriched in para-alkylated amine comprising the step of, at elevated temperature, reacting a para-alkylatable aromatic amine with an ether co-reactive therewith in the presence of a carbon-supported iron oxide catalyst whereby a portion of said ether para-alkylates the aromatic amine and a substantial portion of the remainder of said ether remains undecomposed. The undecomposed ether may be, and preferably is, recovered or recycled to the process.

In particular embodiments of this invention, various iron oxide catalyts are used in which on a weight basis (not counting the weight of any inert support or carrier for the catalyst) the catalyst is composed predominantly of ferric oxide, and contains a minor proportion of an oxide of at least one other metal, for example one or more oxides of germanium, silicon, aluminum, chromium, antimony, indium, and the like, such as $GeO_2$, $SiO_2$, $Al_2O_3$, $Cr_2O_3$, $Sb_2O_3$, $In_2O_3$, etc.

These and still other embodiments of this invention will be apparent from the ensuing description and the appended claims.

DETAILED DESCRIPTION

According to the present invention, a number of ethers have been found to be very effective for selectively alkylating the various aromatic amines in the presence of ferric oxide catalysts. While product selectivity is at least as good as typical processes known to the prior art, in many cases this invention also offers the additional advantage of providing conversion rates somewhat higher than with the corresponding alcohols used according to processes of the prior art. Further, my process provides the advantageous but unexpected result whereby under suitable reaction conditions unreacted ether is not excessively decomposed to uncondensible gases. Rather, most if not all of the ether not consumed in the alkylation reaction remains undecomposed thereby enabling almost complete recovery of the unreacted ether. This of course, makes the recovered ether available for use in another process or for reuse in the present process.

As noted above, one embodiment of this invention involves orthoalkylation of ortho-alkylatable aromatic amines, irrespective of whether the amine is primary, secondary or tertiary. Here the chief requirement as regards the amine is that it has one or both ortho positions substituted by a hydrogen atom.

In another embodiment a primary or secondary aromatic amine is alkylated on the nitrogen atom(s). There are several ways of accomplishing this. One is to use dipropyl ether, diisopropyl ether, or other N-alkylating ether as the alkylating agent. Another way is to employ any suitably reactive ether and a ferric oxide catalyst which during its manufacture was precipitated from an aqueous solution by use of urea. In these cases the alkylated product is enriched in N-alkylated aromatic amine even though it has one or two ortho positions available for alkylation. A third way to accomplish predominant N-alkylation is to use as the reactants a primary or secondary aromatic amine which does not have an ortho position available for alkylation, and any ether co-reactive with such amine, including ethers which normally tend to orthoalkylate ortho-alkylatable aromatic amines. A few typical primary aromatic amines of this type are 2,6-xylidine, 2,6-diethylaniline, 2-ethyl-1-naphthylamine, and 2,3,5,6-tetramethyl-1,4-benzenediamine. Suitable secondary aromatic amines free from excessive steric hindrance of the amino nitrogen atom(s) likewise alkylatable on the amino nitrogen atom(s) are exemplified by N-methyl-2,6-xylidine, N-ethyl-2,6-xylidine, N-methyl-2,6-diethyl-aniline, 1,3-dimethyl-N-methyl-2-naphthylamine, and 9-anthrylamine.

A further embodiment involves para-alkylation of para-alkylatable aromatic amines, irrespective of whether the amine is primary, secondary or tertiary. Here the chief requirement as regards the amine is that it its para position carries a hydrogen atom.

The various embodiments of the present invention are carried out at an elevated temperature conventional for catalytic alkylation processes. The temperature of reaction for the present process is usually about 250° C. or higher, preferably 300° C. or higher. More preferably, the process is carried out at an elevated temperature in the range of about 350°–450° C. While still higher temperatures may be used, the temperature must be selected in accordance with the aromatic amine, catalyst, and ether used for alkylation of the aromatic amine as well as considerations of the process equipment being used. The most preferred temperature range for the preferred reactants of the invention is about 350°–40° C.

When my process is carried out as further described below, then the conversion of aromatic amines such as aniline, o-toluidine, and more complex aromatic amines is usually in the range of from less than 5 to as much as 30% or more. The 30% or more figure is considered very satisfactory for most catalytic alkylation processes. In view of the recoverability of the alkylating agent of the present invention, conversions in this range are especially advantageous since the process can be made much more economical with recovery of such a reactant. My process is suitably carried out at atmospheric pressure but may be carried out at superatmospheric or subatmospheric pressures.

Numerous aromatic amines are usable in the process of this invention. Typical aromatic amines starting materials for the process include the single ring compounds such as aniline, o-toluidine, m-toluidine, p-toluidine, o-ethylaniline, m-ethylaniline, p-ethylaniline, o-isopropylaniline, m-isopropylaniline, p-isopropylaniline, 2,3-xylidine, 2,4-xylidine, 2,5-xylidine, 3,4-xylidine, 3,5-xylidine, 2,3-diethylaniline, 2,4-diethylaniline, 2,5- diethylaniline, 3,4-diethylaniline, 3,5-diethylaniline, 2,3-diisopropylaniline, 2,4-diisopropylaniline, 2,5-diisopropylaniline, 3,5-diisopropylaniline, and the like. Also usable in my process are the N-alkylated aromatic amines such as N-methylaniline, N-ethylaniline, N-isopropylaniline, N,N-dimethylaniline, N,N-diethylaniline, N,N-diisopropylaniline, N-methyl-o-toluidine, N-methyl-2,3-xylidine, N-methyl-2,4-xylidine, N-methyl-2,5-xylidine, N-methyl-3,4-xylidine, N-methyl-3,5-xylidine, N,N-dimethyl-o-toluidine, N,N-dimethyl-m-toluidine, N,N-dimethyl-p-toluidine, N,N-dimethyl-2,3-xylidine, N,N-dimethyl-2,4-xylidine, N,N-dimethyl-2,5-xylidine, N,N-dimethyl-3,5-xylidine, N-ethyl-o-toluidine, N-ethyl-m-ethylaniline, N-ethyl-p-ethylaniline, N-ethyl-2,3-diethylaniline, N-ethyl-2,4-diethylaniline, N-ethyl-2,5-diethylaniline, N-ethyl-3,5-diethylaniline, N,N-diethyl-o-ethylaniline, N-ethyl-3,5-diethylaniline, N,N-diethyl-o-ethylaniline, N,N-diethyl-m-ethylaniline, N,N-diethyl-p-ethylaniline, and the like. Also usable in the process are multiple ring compounds such as 1-naphthylamine, 2-naphthylamine, 1-anthrylamine, 1-phenanthrylamine, and the like. Similarly the aromatic diamines, triamines, and other polyamines are useable. Examples of such compounds include o-phenylenediamine, m-phenylenediamine, p-phenylenediamine, 2,4-toluenediamine, 2,5-toluenediamine, 4,4'-methylenebisaniline, 1,3,5-triaminobenzene, 1,4-diaminonaphthalene, and the like.

Of the above described aromatic amines, the single ring aromatic amines are preferred. Aniline and alkylated anilines are the more preferred compounds of the single ring aromatic amines. Most preferred are aniline and o-toluidine.

In the N-alkylation embodiments of this invention primary and secondary aromatic amines of the type illustrated above may of course be used. Additionally, primary and secondary aromatic amines having no alkylatable ortho position may be used, such as 2-ethyl-6-methylaniline, 3,6-dimethyl-1,2-benzenediamine, 3,5-diethyltoluene-2,4-diamine, 3,5-diethyltoluene-2,6-diamine, 1,3-di-methyl-2-naphthaleneamine, and the like. And in the paraalkylation embodiments of this invention aromatic amines as illustrated above having an alkylatable para position relative to an amino group (primary, secondary, tertiary) may be used. A few additional illustrations include diphenylamine, triphenylamine, N,N,2,6-tetramethylaniline and 2-ethyl-1-naphthaleneamine.

The aromatic amines used in the practice of this invention may contain innocuous ring substituents, i.e., substituents that do not interfere with the alkylation reaction being conducted. Such substituents include halogen atoms, nitro, hydroxyl, hydrocarbyloxy (e.g., alkoxy, phenoxy, etc.), carbonyl groups (e.g., formyl, acetyl, benzoyl, etc.), carboxy groups (e.g., —COOH, —COOR, etc.), tertiary amino groups, and the like.

Various ethers and mixtures of ethers are usable according to the present invention. These include hydrocarbyl ethers having at least one and preferably two methyl, ethyl, propyl or isopropyl groups in the molecule. Besides dimethyl ether, diethyl ether, and dipropyl ether—which are the most preferred alkyl ethers because of their high reactivities and the high selectivity of the products formed from their use—it is possible to employ straight chain dialkyl ethers (e.g., methyl ethyl ether, methyl propyl ether, methyl butyl ether, ethyl propyl ether, ethyl butyl ether, propyl butyl ether, etc.), branched chain dialkyl ethers (e.g., diisopropyl ether, methyl isopropyl ether, methyl isobutyl ether, methyl t-butyl ether, ethyl sec-butyl ether, di-sec-butyl ether, etc.), mixed cycloalkyl alkyl ethers (e.g., methyl cyclopropyl ether, methyl cyclobutyl ether, ethyl cyclohexyl ether, etc.), mixed alkyl aryl ethers (e.g., methyl phenyl ether, ethyl phenyl ether, etc.), mixed alkyl aralkyl ethers (e.g., methyl benzyl ether, ethyl benzyl ether, etc.), and other ethers which are co-reactive with the aromatic amine used in the process.

Also usable in my process are cyclic ethers including those which have one oxygen in the ring as well as those which have more than one oxygen in the ring. These include tetrahydrofuran and oxetane as well as ring alkylated congeners thereof; 1,2-epoxides (ethylene oxide, 1,2-propylene oxide, 1,2-butylene oxide, 2,3-butylene oxide, etc.); 1,4-dioxane, 1,3-dioxolane, and the like. Other candidate materials include dihydrofuran and ring alkylated congeners thereof, trioxane, and the like.

Diaralkyl ethers are suitable for use in the process of this invention. These are exemplified by such compounds as dibenzyl ether, di-phenethyl ether, and the like.

Unsaturated ethers such as diallyl ether are reactive in the process and tend to produce a wide range of products.

Cycloalkylalkyl ethers are deemed usable in the process. These are typified by bis(cyclopropylcarbinyl) ether and bis(2cyclopentylethyl) ether. Still other candidates for use in the process are the glycol ethers such as the ethylene glycol ethers and propylene glycol ethers including 1,2-dimethoxyethane (monoglyme), 1,2-diethoxyethane, 1,2-dimethoxypropane, 1,3-diethoxypropane, and the like. Based on the experimental evidence available to date, glycol ethers appear to require relatively high reaction temperatures and give relatively low conversions of aromatic amine.

Although effective as alkylating agents, acetal compounds—i.e., non-cyclic compounds having two ether linkage oxygens connected to the same carbon atom—are not suitable for use in the process of this invention as they undergo extensive decomposition to non-condensible gases. That is, the portion of such acetals not consumed in alkylating the aromatic amine tends to be extensively if not totally decomposed.

A surprising feature of this invention is that both dimethyl ether and diethyl ether have a strong tendency to alkylate ortho-alkylatable aromatic amines in the ortho position, whereas dipropyl ether and diisopropyl ether exhibit a strong tendency to alkylate ortho-alkylatable primary aromatic amines on the nitrogen atom. Presumably this sharp difference in mode of reaction has something to do with the nature or structure of the transitory intermediate(s) formed in the reaction. However no definitive explanation can be offered at this time.

It is important when practicing my invention to utilize an ether which is co-reactive with the aromatic amine reactant in the presence of the catalyst and under the reaction conditions being used in any given reaction. For example, in runs conducted at 350°, 400° and 450° C. dibutyl ether gave no reaction with aniline, and yielded only gaseous ecomposition products at the two higher temperatures. On the other hand with the same ferric oxide-germanium dioxide catalyst, aniline was sucessfully alkylated by di-sec-butyl ether at 350° and 400° C. Attempts to alkylate aniline with tetrahydropy an at 350° and 400° C. over this same catalyst proved unsuccessful.

It is also important to insure that the catalyst being used is sufficiently active to enable the particular alkylation reaction desired to proceed. For example as noted above, di-sec-butyl ether successfully alkylated aniline at 350° and 400° C. over a ferric oxide-germanium oxide catalyst (Catalyst A hereinafter). With an apparently less active ferric oxide-antimony oxide catalyst (Catalyst D hereinafter), di-sec-butyl ether failed to react with aniline at either 350° or 400° C. whereas reaction with diethyl ether proceeded smoothly over that same Catalyst D at 350° C. Likewise at 350 and 400° C., diallyl ether did not react with aniline over a 96.1% ferric oxide-3.9% germanium dioxide catalyst prepared in essentially the same way as Catalyst C (note Example I hereafter) except that the FeOOH catalyst precursor (also referred to as $Fe_2O_3.H_2O$) as precipitated from aqueous solution was allowed to stand for ten days in contact with the mother liquor before resuming the rest of the preparative procedure. At both temperatures only decomposition of the diallyl ether was observed. On the other hand when the same reactants were passed over a 96.1% ferric oxide-3.9% germanium dioxide catalyst (Catalyst A hereinafter), alkylation was effected at 350° and 400° C.

In separate runs FeO and $Fe_3O_4$ catalysts available from commercial suppliers gave no reaction between diethy ether and aniline at 350°, 400° and 450° C. It is not known whether these results signify that the FeO and $Fe_3O_4$ forms of iron oxide are incapable of serving as viable catalysts in the process of this invention or whether the results merely signify that the particular samples or types of FeO and $Fe_3O_4$ were not suitably active for use in the practice of this invention.

The present invention is capable of being carried out in either a batch or continuous operation mode according to the available equipment and intentions of the operators.

According to the invention, various catalysts may be used so long as the catalyst includes a sufficient amount of catalytically active iron oxide to cause the alkylation to proceed under suitable reaction conditions. Preferably, the catalyst has the active iron oxide as a main constituent thereof, although appropriate mixed metal oxides in which the iron oxide component is as low as 30% by weight of the mixture may be used. Numerous catalyst compositions are available for use according to the present invention. Generally, a combination of catalytically active iron oxide and a second metal oxide is used as the catalyst material. This combination may optionally include still other additional materials, preferably metal oxides. The various metal oxides usable with the iron oxide catalysts include the oxides of alkali metals, alkaline earth metals, aluminum, chromium, magnesium, manganese, molybdenum, ruthenium, silicon, tungsten, and various combinations of these. A preferred catalyst combination is that of the iron oxide with germanium oxide. A suitable method for preparation of such a catalyst is given in the examples below.

The iron oxide catalysts may be prepared by any of the various means known in the art, provided of course that the resultant catalyst has suitable activity for the alkylation reaction at hand. The catalyst may be formed as a precipitate or as an extrusion, or may in the alternative be prepared on a support. Generally, I have found that the use of a precipitate or unsupported catalyst is superior for the process of the present invention. Various other oxides usable as additional components of the catalyst of the present invention such as gallium oxide, germanium oxide, yttrium oxides, niobium oxides, titanium dioxide, zirconium dioxide, hafnium dioxide, tantalum oxides, bismuth oxides, tin oxides, and the like may be prepared by any of the known means and combined with the iron oxide according to the invention. One of germanium oxide and chromium oxide are preferred as at least one of the additional metal oxides of the invention where more than just iron oxide catalyst is used.

The preferred mixed oxide catalysts should contain one or more iron oxides, most preferably ferric oxide, as the principal active component (i.e., catalytic material as distinguished from inert support or the like) and lesser quantities of one or more other metal oxides (e.g., 40% ferric oxide, 30% alumina, and 30% silica). Preferably the catalysts contain on a weight basis over 50% of one or more catalytically active iron oxides and a minor proportion of one or more oxides of one or more other metals. Particularly preferred catalysts are exemplified by catalysts containing by weight at least 85% ferric oxide and up to 15% of one or more of $GeO_2$, $SiO_2$, $Al_2O_3$, $Cr_2O_3$, $Sb_2O_3$, $TiO_2$, $ZrO_2$, $HfO_2$, $MoO_3$, $WO_3$, etc.

The supported iron oxide catalysts used in forming alkylated aromatic amines enriched in the para-alkylated product are similar to the orthoalkylation and N-alkylation catalysts described above, except they are supported on elemental carbon, usually in granular, pellet or finely-divided form, whereby the catalyst has a para-directing capability. While the amount of carbon in the catalyst may vary depending on the composition and characteristics of the iron oxide catalyst, generally speaking the catalyst will contain up to about 30% (preferably up to about 20%) by weight of the metal oxide(s) based on the total weight of the catalyst (metal oxide(s) plus carbon support). Suitable forms of carbon are derived from a variety of sources. Good results have been achieved using amorphous carbon.

The process of this invention is capable of producing a variety of alkylated aromatic amines. For example, 2,6-dimethylaniline may be prepared most conveniently from o-toluidine by reaction with dimethyl ether. Similarly, 2,6-diethylaniline may be prepared from o-ethylaniline using diethyl ether or p-dioxane (or both) as the alkylating agent. To co-produce o-butylaniline and 1-phenylpyrrole, it is desirable to react tetrahydrofuran with aniline. Synthesis of N-propylaniline is readily accomplished by reacting dipropyl ether with aniline. And formation of p-toluidine from aniline and dimethyl ether is readily achieved pursuant to this invention by using a carbon-supported catalyst.

The present invention is further illustrated by the following examples of the best mode of the invention of which I am now aware, in which all of the percentages are expressed on a weight basis unless otherwise specified.

EXAMPLE I

Catalyst Preparation

Catalyst A

A catalyst, hereinafter referred to as "A", was prepared as follows: About 202 grams of $Fe(NO_3)_3.9H_2O$ was dissolved in two liters of distilled water. The slow addition of 14.5N $NH_4OH$ resulted in the formation of a precipitate. The $NH_4OH$ addition was continued until the pH was adjusted to 7. The precipitate was filtered, washed and dried at 110° C. Germanium tetraethoxide (about 3.91 grams) was dissolved in 25 milliliters of ethanol. The dry precipitate FeOOH was impregnated with the germanium solution and the ethanol was evaporated at 110° C. Water was added to hydrolyze the germanium tetraethoxide and the precipitate was air dried, then calcined at 450° C. for 12 hours.

Catalyst B

A second catalyst hereinafter referred to as "B" was prepared in similar fashion by dissolving 202 grams of Fe(NO$_3$)$_3$.9H$_2$O in two liters of distilled water. The precipitate formed by slowly adding 14.5N NH$_4$OH. The pH was then adjusted to seven. The precipitate was filtered and washed. The paste-like precipitate was extruded to give 1/16th inch diameter extrusions which were air dried and then oven dried at 110° C. About 3.9 grams of germanium tetraethoxide were then dissolved in 25 milliliters of ethanol and used to impregnate the extrusions. The ethanol was evaporated at about 110° C. in an oven. The extrusions were wetted with distilled water to hydrolyze the germanium tetraethoxide. The extrusions were then oven dried at 110° C. and calcined at 450° C. for 24 hours.

Catalyst C

A third catalyst hereinafter referred to as catalyst "C" was prepared by dissolving 202 grams of Fe(NO$_3$)$_3$.9H$_2$O in two liters of distilled water. A precipitate formed by slowly adding 14.5N NH$_4$OH and the pH was adjusted to 7. The precipitate was filtered, washed, and extruded to give 1/16th inch diameter extrusions. The extrusions were air dried overnight and about 3.91 grams of germanium tetraethoxide, dissolved in 20 milliliters of ethanol, was used to impregnate the extrusions. The ethanol was evaporated under a dry nitrogen stream. Water was added to hydrolyze the germanium tetraethoxide and the water was then evaporated under a dry nitrogen stream. The extrusions were oven dried at 110° C. for two hours and then calcined at 450° C. for an additional twelve hours.

Apparatus and Procedure

A tubular reactor was fabricated to fit within an Ohio Thermal wire wound tubular furnace, model TllC-0432. The muffle tube of the furnace was 1½ inches inside diameter and 12 inches long, constructed of fused alumina. A ¼ inch inside diameter thermocouple well was provided adjacent to the heating element. The thermocouple was used to control the series 4DA controller which has a range of 200°–1100° C. The reactor was a 19 inch long, 1 inch inside diameter stainless steel tube fitted with an internal thermocouple well. The reactor tube was fitted for supply of helium gas from one line and a second line with a Milton Roy pump therein. The second line fed reactants from a reservoir attached thereto. A water condenser below the reactor tube and an ice bath were used to collect liquid in glassware in the ice bath. The vapors transmitted from the glassware in the ice bath were directed to a dry ice bath and the outlet thereof was connected directly to a gas chromatography unit and then to a wet test meter.

The following procedure was used for all of the runs of the invention and the comparative runs given in the tables below. The reactor tube was filled with 5 millimeter glass beads to define the catalyst bed location. A weighed amount of catalyst was then supplied to the catalyst bed area and additional 5 millimeter beads were used to fill the tube to the top of the furnace. All equipment was properly purged and flushed according to standard laboratory practice. The desired feed of the runs given in the table below was added to the reservoir and the pump and inlet tube as necessary. The ice water bath and dry ice bath were attached and the helium flush was started at the rate of 20–30 cc per minute during furnace warmup and stabilization. To start a run, the helium was turned off, and the feed pump was turned on at the desired feed rate. The thermocouple temperatures were recorded along with the feed level and the wet test meter readings. The sampling times were also noted. The product gases were directed to the sample loop of the GC sampling valve and injected onto a 10'×⅛" Poropak ™ R column. The traps were removed and immediately replaced with a second set. The liquid samples were combined and weighed. To terminate the run, the feed pumps were turned off and drained for about five minutes before removing the residue therein. Thereafter, the helium flush was again turned on at about 20–30 cc per minute and the furnace was turned off. After cooling to room temperature, the reactor tube was removed for catalyst inspection, analysis, and/or replacement. An inert support was not used in any of the runs of Table I below. For all of the runs, a liquid hourly space velocity (LHSV) of 0.2 hr.$^{-1}$ was used, unless otherwise specified.

Table I sets forth the results of a series of runs in which Catalysts A, B and C were used with ethers pursuant to this invention, and with alcohols according to the prior art. In addition, Table I presents the results of a run in which acetal was used as the alkylating agent.

In Table I the following abbreviations are used:
Alk. Agt.—Alkylating Agent
Cat.—Catalyst
(Me)$_2$O—Dimethyl Ether
(Et)$_2$O—Diethyl Ether
(Pr)$_2$O—Dipropyl Ether
THF—Tetrahydrofuran
Dioxane—1,4-Dioxane
MeOH—Methanol
EtOH—Ethanol
Acetal—Diethyl Acetal

TABLE I

| Run No. | Alk. Agt. | Mole Ratio Aniline to Alk. Agt. | Reaction Temp., °C. | Gaseous Reaction Product, l./hr. | Unreacted Alk. Agt % | Ortho-Alkylated Product, % | Cat. |
|---|---|---|---|---|---|---|---|
| 1 | (Me)$_2$O | 1:2.5 | 350 | — | 95 | 100 | A |
| 2 | (Et)$_2$O | 1:2.5 | 350 | .18 | 90 | 72 | A |
| 3 | (Et)$_2$O | 1:2.5 | 400 | .76 | 60 | 71 | A |
| 4 | (Et)$_2$O | 1:2.5 | 350 | .11 | 90 | 55 | B |
| 5 | (Pr)$_2$O | 1:1 | 350 | .14 | 99 | 57* | B |
| 6 | THF | 1:3 | 350 | .13 | 90 | 28** | A |
| 7 | THF | 1:3 | 400 | .66 | 60 | 23** | A |
| 8 | Dioxane | 1:2 | 350 | .13 | 85 | 67 | C |

TABLE I-continued

| Run No. | Alk. Agt. | Mole Ratio Aniline to Alk. Agt. | Reaction Temp., °C. | Gaseous Reaction Product, l./hr. | Unreacted Alk Agt % | Ortho-Alkylated Product, % | Cat. |
|---|---|---|---|---|---|---|---|
| 9 | Dioxane | 1:2 | 400 | .45 | 95 | 51 | C |
| 10* | MeOH | 1:5 | 350 | 2.11 | 0 | 88 | A |
| 11 | EtOH | 1:5 | 350 | 1.80 | 0 | 51 | A |
| 12 | EtOH | 1:5 | 350 | 1.67 | 5 | 32 | B |
| 13 | EtOH | 1:5 | 350 | 1.02 | 10 | 69 | A |
| 14 | Acetal | 1:2 | 350 | 1.41 | 2 | 47 | A |

*In this run N—akylation occurred; the main product was N—propyl aniline (product distribution, wt %: 56.3 N—propylaniline, 7.6 N—isopropyl aniline, the balance being others).
**A comparable yield of 1-phenylpyrrole was also obtained.
***The LHSV in this run was 0.7 hr.$^{-1}$.

The advantages and unexpected results of the present invention over the processes of the prior art are readily apparent from a review of the above Table I and comparison of the appropriate values for runs according to the invention (1–9) and runs of the prior art (10–13). It is readily apparent by comparing the amount of gaseous reaction products, expressed above as liters per hour, that in general the process of this invention resulted in the production of small amounts of gaseous by-products. Naturally, in the case of Run 1, where dimethyl ether was used as the alkylating agent, the effluent from the reactor contained a substantial amount of unreacted gaseous dimethyl ether. Dimethyl ether is of course itself a gas at room temperature but in this case it was found, in accordance with the advantages of the present invention, that greater than 95% of the unreacted alkylating agent (here a gas) was recoverable.

All of the comparative runs using an alkylating agent of the prior art (Runs 10–13) or diethyl acetal (Run 14) resulted in the production of at least one full liter of gaseous by-product per hour. Furthermore, these runs resulted in almost complete decomposition of the alkylating agent. Moreover, all of the runs carried out according to the present invention resulted in selective production of desirable alkylated products.

A similar comparison can be made between the above runs of the invention and Runs 10–14, by observing the amount and make-up of liquid which is condensed and collected in the traps. For the runs of the present invention in which a liquid alkylating agent was used, the amount of liquid was quite large in comparison to the amount of liquid where an alcohol or diethyl acetal was used as the alkylating agent. In most cases substantially all of the unreacted ether was recoverable. In addition, in the runs of the present invention the by-products were chiefly carbon monoxide, carbon dioxide, hydrogen, and some water. In comparison, the runs according to the prior art and with diethyl acetal resulted in the additional production of significant amounts of $C_1$–$C_4$ hydrocarbons as well as smaller amounts of carboxylic acids, esters, and the like.

Similar runs have been carried out in accordance with the prior art wherein o-toluidine was reacted with methanol using an iron oxide-germanium oxide catalyst prepared similarly to the manner described above. While such runs provided a yield of 2,6-dimethylaniline, substantially all of the methanol not used to alkylate the o-toluidine was decomposed.

While the process of Runs 1–9 given above used preferred $GeO_2$-promoted catalysts, other experiments which have been carried out indicate that the ferric oxide catalyst alone is sufficient to result in some alkylation with good recovery of ether not consumed for alkylation.

EXAMPLE II

Catalyst Preparation

Catalyst D

Concentrated ammonia was slowly added to 19.8 g of $Fe(NO_3)_3.9H_2O$ dissolved in 1 liter of water until the pH reached 7. The precipitate which formed during this time was filtered off using a Buchner funnel, washed with water and allowed to stand overnight. To the resultant gel was added $Sb_2O_3$ powder (0.25 g) and these were mixed thoroughly in a mortar and pestle. The gelatinous product was extruded through a 50 cc plastic syringe and air dried over a weekend. It was then dried in an oven at 110° C. for two hours and calcined at 450° C. for six hours yielding 19.1 g of finished catalyst. Its composition corresponded to 98.7% $Fe_2O_3$ and 1.3% $Sb_2O_3$.

Catalyst E

In 2.25 liters of distilled water were dissolved 202.0 g of $Fe(NO_3)_3.9H_2O$, 14.66 g of $In(NO_3)_3.5H_2O$ and 2.0 g of $Cr(NO_3)_3.9H_2O$. Concentrated ammonia was added with stirring to a pH of 7. The precipitate which formed was filtered, washed and extruded through a 50 cc plastic syringe. After drying in air, the material was dried in an oven at 100° C. for two hours and calcined at 450° C. for six hours thereby yielding 46.7 g of finished catalyst of the composition 86.4% $Fe_2O_3$, 12.6% $In_2O_3$ and 1.1% $Cr_2O_3$.

Catalyst F

Concentrated ammonia was gradually added to a solution of 100 g of $Fe_2O_3.9H_2O$ and 52.5 g of uranyl acetate dihydrate, $(CH_3COO)_2UO_2.2H_2O$, in 1 liter of distilled water. The precipitate was recovered by filtration on a Buchner funnel, washed with water and allowed to stand overnight. The gel was then extruded through a 50 cc plastic syringe and air dried over a weekend. The product was then oven dried at 100° C. for two hours and calcined at 450° C. for six hours. This yielded 53.9 g of finished catalyst of the composition: 37.2% $Fe_2O_3$ and 62.8% $UO_2$.

Apparatus and Procedure

The reactants in these runs were diethyl ether and aniline (2.5:1 mole ratio, respectively) and the apparatus and procedure were the same as in Example I. Table II presents the results of these runs.

TABLE II

| Run No. | Orthoalkylation of Aniline | | | |
|---|---|---|---|---|
|  | 15 | 16 | 17 | 18 |
| Catalyst | D | E | F | F |

TABLE II-continued

| | Orthoalkylation of Aniline | | | |
|---|---|---|---|---|
| Run No. | 15 | 16 | 17 | 18 |
| Temperature, °C. | 350 | 400 | 350 | 400 |
| Aniline conversion, % | 6.5 | 11 | 1 | 1 |
| Product Distribution, % | | | | |
| o-Ethyl aniline | 62.9 | 45.1 | 1* | 1* |
| m-Ethyl aniline | — | 8.1 | — | — |
| Diethyl aniline | — | 5.4 | — | — |
| Others | 37.1 | 41.4 | — | — |
| Gaseous Products, mL/hr | 100 | 735** | 300 | 665 |

*o-Ethyl aniline was the only product detected.
**Under the same reaction conditions ethanol produced 2195 mL/hr In runs made as in Table II in which several commercially available iron oxides were used as the catalyst, no reaction occurred between diethyl ether and aniline (mole ratio 2.5:1 respectively). The catalysts and the temperatures used were as follows:

$Fe_3O_4$ pellets (Harshaw Fe-X-L3261-31-8 T ⅛)—350°, 400° & 450° C.

FeO powder (Alfa Products)—350°, 400° & 450° C.

$\gamma$-$Fe_2O_3$ powder (Alfa Products)—300°, 350°, 375° & 400° C.

EXAMPLE III

Catalyst Preparation

Catalyst G

Ferric nitrate (202 g $Fe(NO_3)_3 \cdot 9H_2O$, Baker Reagent Grade) was dissolved in 2 liters of distilled water with stirring. Then 200 g of urea (98% grade from Aldrich) was dissolved in the ferric nitrate solution. The solution was heated to boiling and maintained at a slow boil until the precipitation of the iron product appeared complete—pH 7. The solids were filtered off on a Buchner funnel, and washed twice with distilled water. The paste-like mass was extruded through a 50 cc syringe to give 1/16 inch extrusions. These were dried in an oven at 110° C. The dried extrusions were then treated to incipient wetness with a solution of 3.91 g of germanium tetraethoxide in 25 mL of ethanol. The ethanol was evaporated off in an oven at 110° C. Then water was added to the extrusions to incipient wetness to hydrolyze the germanium tetraethoxide. The extruded catalyst was then dried in an oven at 110° C. followed by calcining overnight at 450° C. The procedure resulted in 37.6 g of an iron oxide-germanium dioxide catalyst of the composition: 96.1% $Fe_2O_3$ and 3.9% $GeO_2$.

Catalyst A was also used in the following runs, and its synthesis is described in Example I.

Apparatus and Procedure

The reactants in these respective runs were aniline and diethyl ether, diisopropyl ether, 1,3-dioxolane and the dimethyl ether of diethylene glycol. The apparatus and procedure were the same as in Example I except as otherwise indicated in Table III, which presents the results of these runs. The following abbreviations are used in Table III:

DE—diethyl ether
DIP—diisopropyl ether
1,3-D—1,3-dioxolane
DMDG—dimethyl ether of diethylene glycol

TABLE III

| | N—Alkylation of Aniline | | | | |
|---|---|---|---|---|---|
| Run No. | 19 | 20 | 21 | 22 | 23 |
| Catalyst | G | A | A | A | A |
| Temperature, °C. | 350 | 350 | 350 | 400 | 400* |
| Ether | DE | DIP | 1,3-D | 1,3-D | DMDG |
| Mole ratio, ether:aniline | 2.5:1 | 2:1 | 2:1 | 2:1 | 1:1 |
| Aniline conversion, % | 19 | 25 | 3 | 13 | 2 |
| Product Distribution, % | | | | | |
| o-Toluidine | — | — | — | 6 | 11 |
| N—Methyl aniline | — | — | 84 | 48 | 65 |
| o-Ethyl aniline | 28.9 | — | — | — | — |
| N—Ethyl aniline | 58.2 | — | — | — | — |
| Diethyl aniline | 2.3 | — | — | — | — |
| o-Isopropyl aniline | — | 16 | — | — | — |
| N—Isopropyl aniline | — | 46 | — | — | — |
| N—Isopropylidene aniline | — | 16 | 12 | — | — |
| Others | 10.6 | 22 | 4 | 46 | 24 |
| Gaseous Products, mL/hr | 130 | 220 | 80 | 610 | 60 |

*At 350° C. no reaction occurred and no gaseous decomposition products were formed In runs conducted as in Table III wherein di-n-butyl ether and aniline were employed with the same catalyst in a molar ratio of 1:1 no reaction occurred at 350°, 400° and 450° C. At 350° C. no gaseous decomposition products were formed. At 400° C. gaseous decomposition products were formed at the rate of 75 mL/hr. At 450° C. this rate was 310 mL/hr. In contrast, when using the same catalyst di-sec-butyl ether did react with aniline in runs conducted at 350° C. and at 400° C. using a mole ratio (ether:aniline) of 2:1. At 350° C. the aniline conversion was 5%; at 400° C., 4%. In both cases sec-butyl aniline was the only product detected. It was probably N-sec-butyl aniline, although this was not confirmed.

Similar runs were conducted using the same catalyst and tetrahydropyran and aniline (3:1 mole ratio, respectively) at 350 and 400° C. No alkylation reaction occurred in either case. At 350° C. no gaseous decomposition products were formed. At 400° C. gaseous decomposition products were formed at the rate of 30 mL/hr. When diallyl ether and aniline were reacted in a 2:1 mole ratio over the same catalyst at 350° and 400° C. alkylation reactions occurred. The aniline conversions were 20% at 350° C. and 38% at 400° C. In both cases a wide range of products was formed. The main products identified by GC-MS in the 400° C. run were N-methyl aniline, propyl aniline, quinoline and propylquinoline.

EXAMPLE IV

Using the apparatus and procedure of Example I, aniline was alkylated with dibenzyl ether using Catalyst A. The reactants were introduced to the catalyst in a mole ratio of 2 moles of dibenzyl ether per mole of aniline. The data are presented in Table IV.

TABLE IV

| N—Alkylation of Aniline with Dibenzyl Ether | | |
|---|---|---|
| Run No. | 24 | 25 |
| Temperature, °C. | 350 | 400 |
| Aniline conversion, % | 55 | 100 |
| Product Distribution, % | | |
| N—Benzylidene aniline | 93 | 97 |
| Others | 7 | 3 |
| Benzyl ether conversion, % | 27 | 82 |
| Product Distribution, % | | |
| N—Benzylidene aniline | 41 | 40 |
| Benzene | — | 3 |
| Toluene | 55 | 48 |
| Benzyl alcohol | 1 | 8 |

TABLE IV-continued

| N—Alkylation of Aniline with Dibenzyl Ether | | |
|---|---|---|
| Run No. | 24 | 25 |
| Others | 3 | 1 |
| Gaseous Products, mL/hr | None | 30 |

It will be noted from Table IV that with dibenzyl ether there is a strong tendency for the nitrogen atom of aniline to be substituted with a benzylidene group ($C_6H_5CH=$).

When the procedure of Example IV was repeated in exactly the same fashion except that diphenyl ether was substituted for dibenzyl ether, no reaction occurred at 400° and 450° C.

EXAMPLE V

This example illustrates the para-alkylation selectivity achievable in the practice of this invention using a carbonmodified iron oxide catalyst.

The catalyst was prepared in the following manner: A solution of 6.33 g of $Fe(NO_3)_3.9H_2O$ dissolved in 75 mL of water was added to 47.5 g of activated carbon pellets (Alfa Products, Grade 3LXC, 6-8 mesh, Lot 022674). The water was evaporated from the mixture at low heat on a hot plate. The mixture was further dried in an oven at 100° C. for three hours. The mixture was then calcined at 350° C. for four hours and cooled to room temperature. The iron oxide-carbon product was then treated with a solution of 0.236 g of germanium tetraethoxide dissolved in 70 mL of ethanol. Then distilled water (20 mL) was added in order to hydrolyze the germanium tetraethoxide, and the mixture was well stirred. The ethanol and water were evaporated off from the catalyst at low heat using a hot plate. Further drying was accomplished overnight in an oven at 100° C., and was followed by calcining at 350° C. for seven hours. The resultant catalyst was composed of 5.0% $Fe_2O_3$ and 0.2% $GeO_2$ supported on activated carbon.

Using the procedure and apparatus as described in Example I, aniline was ethylated with diethyl ether at 350° C. using this carbon-modified $Fe_2O_3$-$GeO_2$ catalyst. The aniline conversion was 7% and the non-condensable gaseous decomposition products were formed at the rate of only 60 mL/hr. The product distribution was indicated by GC-MS was 42.0% p-ethyl aniline, 17.7% o-ethyl aniline and 8.0% N-ethyl aniline, the balance being other products.

It is possible to vary certain aspects and other features of the above described invention without departing from the lawful scope or true spirit thereof.

What is claimed is:

1. A process for alkylating an aromatic amine which comprises reacting at elevated temperature and in the presence of an iron oxide alkylation catalyst, an alkylatable aromatic amine with an ether co-reactive therewith whereby a portion of said ether alkylates the aromatic amine and a portion of said ether remains undecomposed.

2. The process of claim 1 further comprising recovering some or all of said portion of undecomposed ether.

3. The process of claim 1 wherein the elevated temperature is at least about 300° C.

4. The process of claim 1 wherein said aromatic amine is a single ring compound.

5. The process of claim 1 wherein said ether is a dialkyl ether having up to 3 carbon atoms in each alkyl group.

6. The process of claim 1 wherein said ether is dimethyl ether or diethyl ether.

7. The process of claim 1 wherein said aromatic amine is aniline, a ring-alkylated aniline, an N-alkylated aniline, or a ring- and N-alkylated aniline and said ether is dimethyl ether or diethyl ether.

8. The process of claim 1 wherein said ether is tetrahydrofuran or a ring-alkylated congener thereof.

9. The process of claim 1 wherein said ether is a diaralkyl ether.

10. The process of claim 1 wherein said ether is dibenzyl ether.

11. The process of claim 1 wherein said ether is dipropyl ether or diisopropyl ether.

12. The process of claim 1 wherein said ether is 1,4-dioxane.

13. The process of claim 1 wherein said ether is 1,3-dioxolane or a ring alkylated congener thereof.

14. The process of claim 1 conducted at a temperature in the range of about 350°-400° C. wherein said ether is dimethyl ether or diethyl ether and said aromatic amine is aniline, o-toluidine, or o-ethylaniline.

15. The process of claim 1 wherein the process is performed as a vapor-phase process.

16. The process of claim 1 wherein said catalyst comprises ferric oxide.

17. The process of claim 16 wherein said catalyst additionally contains at least one additional metal oxide catalyst promoter.

18. The process of claim 17 wherein said catalyst promoter is germanium dioxide.

19. The process of claim 16 wherein said aromatic amine is an N-alkylatable aromatic amine and wherein the ferric oxide catalyst is a urea-precipitated ferric oxide catalyst.

20. The process of claim 19 wherein said N-alkylatable aromatic amine has a hydrogen in at least one of its ortho positions.

21. The process of claim 16 wherein said aromatic amine is a para-alkylatable aromatic amine and wherein the ferric oxide catalyst is supported on carbon.

22. The process of claim 21 wherein said para-alkylatable aromatic amine has a hydrogen in at least one of its ortho positions.

23. The process of claim 22 wherein said para-alkylatable aromatic amine is a primary aromatic amine.

24. A process for ortho-alkylating an aromatic amine having a hydrogen in at least one of the ortho positions, said process comprising (i) flowing said amine along with an orthoalkylating ether co-reactive therewith typified by dimethyl ether, diethyl ether, tetrahydrofuran and 1,4-dioxane, over an orthoalkylation-promoting catalyst comprising a catalytically active iron oxide at a temperature in the range of about 300°-500° C. whereby a portion of said ether orthoalkylates said amine and a portion of said ether passes over said catalyst undecomposed, and (ii) recovering the ortho-alkylated amine and the undecomposed ether.

25. The process of claim 24 wherein the undecomposed ether is recycled in the process.

26. The process of claim 24 wherein said aromatic amine is aniline, o-toluidine or o-ethylaniline.

27. The process of claim 24 wherein the elevated temperature is at least about 300° C.

28. The process of claim 24 wherein said aromatic amine is a single ring compound.

29. The process of claim 24 wherein said ether is dimethyl ether or diethyl ether.

30. The process of claim 24 wherein said aromatic amine is aniline, a ring-alkylated aniline, an N-alkylated aniline or a ring- and N-alkylated aniline and said ether is dimethyl ether or diethyl ether.

31. The process of claim 24 wherein said ether is tetrahydrofuran or a ring-alkylated congener thereof.

32. The process of claim 24 wherein said ether is 1,4-dioxane.

33. The process of claim 24 conducted at about 350°–400° C. wherein said ether is dimethyl ether or diethyl ether and said aromatic amine is aniline, o-toluidine, or o-ethylaniline.

34. The process of claim 24 wherein said catalyst comprises ferric oxide.

35. The process of claim 34 wherein said catalyst additionally contains at least one additional metal oxide catalyst promoter.

36. The process of claim 35 wherein said catalyst promoter is germanium dioxide.

37. The process of claim 36 wherein said catalyst consists essentially of at least about 85 weight percent of ferric oxide and up to about 15 weight percent of germanium dioxide.

38. The process of claim 37 wherein said catalyst consists essentially of at least about 90 weight percent of ferric oxide and from about 0.5 to about 10 weight percent of germanium dioxide.

39. The process of claim 38 wherein said catalyst is an unsupported catalyst consisting essentially of from about 95 to about 99 weight percent of ferric oxide and from about 1 to about 5 weight percent of germanium dioxide.

* * * * *